(12) United States Patent
Ebrahim et al.

(10) Patent No.: US 6,548,646 B1
(45) Date of Patent: Apr. 15, 2003

(54) REFERENCE CONTROL FOR HIGH-SENSITIVITY C-REACTIVE PROTEIN TESTING

(75) Inventors: Alireza Ebrahim, Aliso Viejo, CA (US); Jayshree Parikh, Diamond Bar, CA (US); Warren Eric Vanderslice, Fullerton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 09/938,409

(22) Filed: Aug. 23, 2001

(51) Int. Cl.[7] .......................... A61K 38/16; C07K 1/16
(52) U.S. Cl. ..................... 530/415; 530/380; 530/417
(58) Field of Search ................................ 530/380, 415, 530/417

(56) References Cited

U.S. PATENT DOCUMENTS

| | | | | |
|---|---|---|---|---|
| 4,384,954 A | * | 5/1983 | Nakashima et al. | |
| 4,472,303 A | * | 9/1984 | Tanihara et al. | |
| 6,045,699 A | * | 4/2000 | Yazawa et al. | |

FOREIGN PATENT DOCUMENTS

WO     WO 9012632 A1    * 11/1990

OTHER PUBLICATIONS

"Basic Facts About Perlite" accessed on the Internet at www.perlite.org/bfacts.htm on Jun. 19, 2002.*
R. Gambino, "C–Reactive protein, undervalued, underutilized," *Clinical Chemistry* (1997) 43(11): 2017–2018.
F. Haverkate et al., "Production of C–reactive protein and risk of coronary events in stable and unstable angina," *Lancet* (1997) 349: 462–466.
A. Maseri, "Inflammation, atherosclerosis, and ischemic events: Exploring the hidden side of the moon," *The New England Journal of Medicine* (1997) 336: 1014–1016.
P.M. Ridker el al., "Inflammation aspirin, and the risk of cardiovascular disease in apparently healthy men," *The New England Journal of Medicine*(1997) 336: 973–979.
P.M. Ridker et al., "C–reactive Protein and other markers of inflammation in the prediction of cardiovascular disease in women," *The New England Journal of Medicine*(2000) 342: 836–843.
D. Sainato, "C–reactive protein and cardiovascular disease," *Clinical Laboratory News* (2000) 26: 1–10.
W.L. Roberts et al., "Evaluation of four automated highsensitivity C–reactive protein methods: Implications for clinical and epidemiological applications," *Clinical Chemistry* (2000) 46: 461–468.

* cited by examiner

*Primary Examiner*—Jon P. Weber
(74) *Attorney, Agent, or Firm*—Townsend and Townsend and Crew LLP

(57) ABSTRACT

Low-concentration reference controls for C-reactive protein assays are prepared from higher-level starting materials by simple filtration using silica-type filter media formerly used for removing lipids. This process avoids the need for antibodies to capture the protein and resuspend it. Surprisingly, the removal of CRP by the silica-type filter media is selective toward CRP, having little or negligible effect on other proteins in the starting matrix, and accordingly little or negligible change in the total protein content.

8 Claims, 3 Drawing Sheets

REFERENCE CONTROL FOR HIGH-SENSITIVITY C-REACTIVE PROTEIN TESTING

BACKGROUND OF THE INVENTION

1. Field of the Invention

This invention resides in the field of reference controls for analytical determinations of protein levels in human bodily fluids. More specifically, this invention relates to reference controls for C-reactive protein determinations.

2. Description of the Prior Art

Cardiovascular disease is the leading cause of death worldwide. Presently, the only widely accepted indicator of a risk of an adverse cardiovascular event is the cholesterol level, and yet half of all cardiovascular events occur in people with normal plasma lipid levels.

C-reactive protein (hereinafter referred to as "CRP") is a plasma protein that is synthesized in the liver and consists of five identical, non-glycosylated polypeptide subunits that are noncovalently linked to form a disc-shaped pentamer with a molecular weight of about 125,000. CRP is synthesized by hepatocytes in response to cytokines released into the liver by activated leukocytes. CRP is a nonspecific marker of inflammation and its level increases as a result of tissue injury or infection, elevating rapidly within 4 to 6 hours of the onset of acute levels of these conditions. CRP may rise to 25–35 mg/L after surgery, and peak at 30–35 mg/L during acute bacterial infection. In situations of severe trauma, the CRP concentration in plasma rises to 500–1,000 mg/L.

CRP is also a risk indicator for coronary heart disease. Among the various prognostic markers of heart disease, such as serum amyloid A, soluble intercellular adhesion molecule type 1, interleukin-6, homocysteine, total cholesterol, LDL, apolipoprotein B-100, HDL, and ratio of total cholesterol to HDL, CRP is the strongest predictor of cardiovascular events. When apparently healthy adults are tested for CRP, the fourth quartile (upper 25%) of those tested have been shown to have over four times the risk of those in the first quartile (with a confidence level of 95%), a ratio significantly greater than those of each of the markers listed above.

The use of CRP as a predictor of cardiovascular events differs however from its use as a detector of other types of inflammation or tissue injury, or infection, since the increases that indicate a risk of coronary heart disease are significantly lower than the increases associated with other conditions. For coronary heart disease predictions, therefore, high-sensitivity CRP ("hsCRP") detection methods are used. Automated analyzers on which tests for hsCRP can be performed include Dade Behring BN II Plasma Protein System (Dade Behring, Incorporated, Deerfield, Ill., USA), Abbott Laboratories IMx Immunoassay Analyzer (Abbott Laboratories, Abbott Park, Ill., USA), IMMULITE (Diagnostics Products Corporation, Los Angeles, Calif., USA), and IMMAGE (Beckman Coulter, Inc., Fullerton, Calif., USA). The Dade Behring BN II assay utilizes a monoclonal antibody on a polystyrene particle with fixed-time nephelometric measurements. The Abbott IMx assay is a two-site chemiluminescent enzyme immunometric assay with one monoclonal and one polyclonal anti-CRP antibody. The Beckman Coulter IMMAGE assay uses a polyclonal anti-CRP antibody on latex particles with rate nephelometric measurements. The detection limits for these assays range from 0.01 mg/L to 1.0 mg/L, and these instruments must be calibrated for accuracy at CRP concentrations within these ranges, which are below those traditionally measured in clinical laboratories for less sensitive CRP assays.

Because of the high sensitivity of hsCRP assays and the analytical variances that are typically encountered, quality control is important in monitoring the precision and accuracy of the assays and assay instruments. Reference controls are obtained in two ways. In the first, plasma or serum from blood donors is screened to identify units containing suitably low levels of CRP, and the units thus identified are pooled. In the second, CRP is removed from plasma or serum by affinity chromatography using anti-CRP antibodies. Purified CRP is then added to the resulting CRP-depleted base matrix to achieve the particular levels desired. Both of these methods are time-consuming and costly. Screening, for example, requires extensive testing and may not produce units with the low levels desired, or may not yield the volume needed. Selective removal of CRP by affinity chromatography requires separation techniques such as dialysis and chromatography, following by concentration.

SUMMARY OF THE INVENTION

It has now been discovered that low-concentration CRP reference controls can be prepared from higher-level starting materials by simple filtration using silica-type filter media. Biological fluids obtained from normal healthy individuals can be used as the starting materials. This procedure avoids the need for antibodies to capture the protein, and instead uses filter media that have traditionally been used for removing lipids. Surprisingly, the removal of CRP by the silica-type filter media is selective toward CRP, having little or no effect on other proteins in the starting matrix, and accordingly little or negligible change in the total protein content. Notably, the immunoglobulin content is not significantly affected by the filtration, nor are albumins.

Low-level preparations obtained in this manner can be blended with higher-level preparations such as further quantities of the starting material that have not been filtered, to achieve reference controls with intermediate levels of CRP. By preparing blends in a series of different proportions, multiple controls can be obtained that will serve as materials for an accurate control of the assay and instrument over a range encompassing the anticipated sample results. Controls of particular interest in this invention are those with CRP concentrations below the medical decision point, and most particularly those of CRP concentrations that are less than or equal to 1.0 mg/L.

Details of these and other features, embodiments, and advantages of the invention will become apparent from the description that follows.

DETAILED DESCRIPTION OF THE INVENTION

Figure 1:
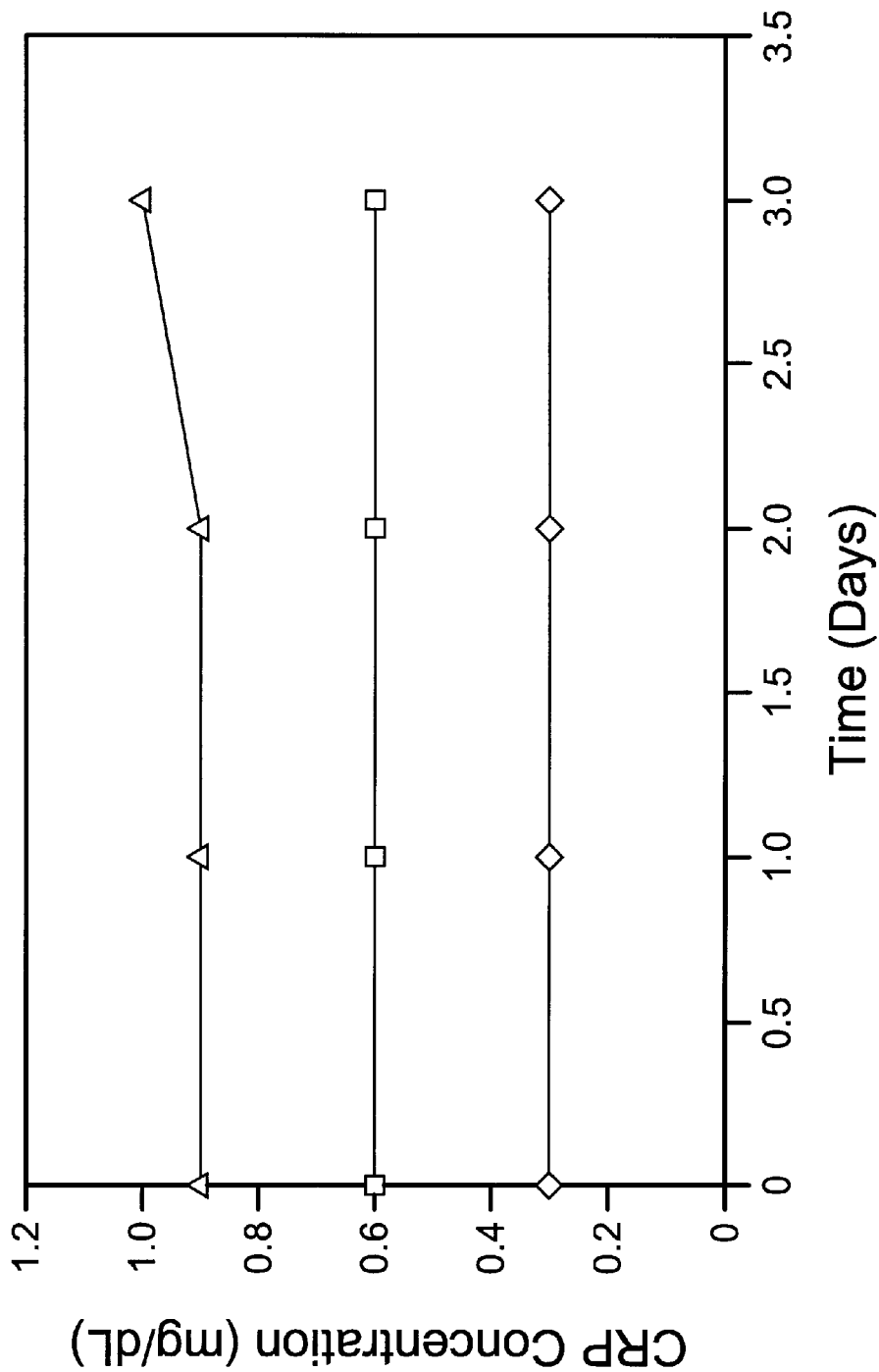
FIG. 1 is a plot of the results of an accelerated stability test of controls in accordance with this invention, taken under closed-vial conditions.

Filter media that can be used in the practice of this invention are silica-type, or silica-containing, media, i.e., media that contain silica in some form, including processed forms, naturally occurring forms, and purified forms. One form of silica that can be used is perlite, which is naturally occurring siliceous rock. Perlite is available commercially from suppliers such as American Perlite Company, Redco II, and Redco International, all with corporate offices in North Hollywood, Calif., USA. Another silica-type medium is fumed silica, available as AEROSIL, a product of Degussa Corporation, Parsippany, N.J., USA. A further example is precipitated silica. Still other forms of silica-type media will be readily apparent to those skilled in the art.

In preferred embodiments of the invention, the silica-type filter medium is supported on a filter support which provides high surface area and structural integrity. Cellulose and cellulose derivatives are examples of suitable supports; others will be readily apparent to those skilled in the filtration and chromatography art. One example of a support silica-type filter is ZETA PLUS®, a cellulose-supported aerosil filter available from Cuno Incorporated, Meriden, Conn., USA. The filter can assume any of the various physical forms in which filters are generally available. Examples are pre-filter cartridges, disks, membranes, pads and capsules. Filtration can also be performed with a slurry filter, followed by solid-liquid separation by simple filtration.

Prior to the silica-based filtration to remove CRP, the starting material (i.e., the base matrix) can be either concentrated or diluted to a particular total protein concentration if desired. This may be desirable if for example the CRP-removal filtration is best performed at a particular concentration or concentration range. Both concentration and dilution can be achieved by methods known in the art. Concentration can be achieved for example by ultrafiltration using ultrafilter membranes with a molecular weight cutoff of 1,000 to allow removal of water and salts, and dilution can be achieved by the addition of saline solution. A typical target concentration of total protein may be within the range of about 3 g/dL to about 10 g/dL.

Adjustment of the pH can also be adjusted to a near-neutral value prior to filtration if the matrix is not already at a near-neutral pH. A preferred final pH range is about 6.5 to about 7.5, or most preferably about 7.0 to about 7.5. Adjustment can be achieved by adding any suitable acid or base that is otherwise inert to the matrix components.

The amount of CRP removed by the filtration is not critical to the invention but will be any amount that reduces the CRP concentration to a level that is suitable to serve as the lowest level control, and that can be blended with higher levels at different proportions to achieve a set of controls at graded concentrations spanning the desired range. In the preferred practice of this invention, the CRP concentration after filtration will be less than 0.1 mg/L, more preferably less than 0.05 mg/L, and most preferably within the range of 0.01 mg/L to 0.05 mg/L. Blending of the filtrate with non-filtered portions will then be done to achieve a range of concentrations of which the unblended CRP-depleted control is the lowest. The range itself will be low enough to detect analytical variances. In general, the range will be below the range of CRP in normal healthy patients, i.e., below 3 mg/L. Three or more concentration levels will preferably be prepared in this manner, ranging for example from below 0.05 mg/L to 3 mg/L, or more preferably from about 0.1 mg/L to about 1.0 mg/L. Once this range of low-level controls is prepared, it can be supplemented with additional controls at higher concentrations, including those that are commercially available. These higher-level controls are generally prepared by adding either native or recombinant CRP to normal human serum rather than extracting CRP from the serum. High-level controls are available for example from Bio-Rad Laboratories, Inc., Calif. USA, under the names LIQUICHEK™ Immunology Control and LYPHOCHEK® Immunology Plus Control.

After filtration of the source material through the silica-type filter, and after blending if blending is performed, an antimicrobial agent can be added to impart stability to the material. Sodium azide is one example of an antimicrobial agent. Other examples are gentamycin, ciprofloxacin, neomycin sulfate, and chloramphenicol. Still further examples will be readily apparent to those skilled in the art. The appropriate amount of antimicrobial agent will be any amount that achieves an antimicrobial effect, i.e., that renders the proteins and other species in the matrix stable against microbial attack. In most cases, suitable amounts will range from about 0.01 mg/dL to about 0.5 mg/dL. Once prepared, the control can be sterile filtered, sealed in an aseptic vial, and frozen until ready for use.

Any human bodily fluid that contains CRP can be used as the starting material. Examples are cerebrospinal fluid, urine, saliva, whole blood, serum, and plasma. Serum and plasma are preferred.

The following example is offered for purposes of illustration and is not intended to limit the scope of the invention.

EXAMPLE

This example illustrates the preparation of CRP-depleted human serum and the blending of the depleted serum with normal human serum to prepare low-concentration controls designed for clinical test methods for hsCRP in concentrations at or below 1.0 mg/L.

Preparation of Normal Human Serum

Units of normal human plasma were pooled and defibrinated according to conventional procedures to form a base serum matrix. The total protein concentration of the matrix was adjusted to 6.0 g/dL by concentrating the matrix or diluting it with normal saline solution. The pH of the matrix was then adjusted to 7.3. The concentration of endogenous CRP in the matrix was then determined by the BN 100 assay of Dade Behring, Incorporated, and an hsCRP assay obtained from Kamiya Biomedical Company (Seattle, Wash., USA). The assays revealed that the concentration of endogenous CRP was 1.1 mg/L.

Preparation of CRP-Depleted Human Serum

Further units of normal human plasma were pooled and defibrinated, the total protein concentration was adjusted to 6.0 g/dL, and the pH adjusted to 7.3, as above. The resulting matrix was then filtered through filter pads or capsules consisting of a precipitated silica or perlite on cellulose, using pressurized filtration housing. The concentration of CRP in the filtrate was then determined as above, and the results indicated that the concentration was below the limit of quantitation of both the BN 100 assay (whose limit was 0.175 mg/L) and the Kamiya hsCRP assay (whose limit was 0.05 mg/L), indicating efficient and successful removal of CRP from the serum base matrix. Lipids and lipid components were also removed in the filtration. This enhanced the clarity and storage stability of the product. Table 1 below lists the levels of CRP and lipid components from a typical serum sample both before and after filtration, with CRP levels as determined by each of the two assays.

TABLE 1

CRP and Lipid Levels in Serum Before and After Filtration

|  | CRP by BN 100 (mg/L) | CRP by Kamiya (mg/L) | Cholesterol (mg/dL) | Triglycerides (mg/dL) | HDL (mg/dL) |
|---|---|---|---|---|---|
| Pre-filtration | 1.1 | 102 | 117 | 75.7 | 30.5 |
| Post-filtration | <0.175 | <0.05 | <3 | <4 | <3 |

Serum protein concentrations, including albumin, immunoglobulin, and total protein, were also determined both before and after filtration, by conventional methods. The results are shown in Table 2, which indicates that the changes were insignificant.

TABLE 2

Serum Protein Levels Before and After Filtration

| Analyte | Units | Pre-filtration | Post-filtration |
|---|---|---|---|
| Total Protein | g/dL | 6.7 | 6.4 |
| Albumin | g/dL | 3.8 | 3.8 |
| Immunoglobulin G | mg/dL | 957 | 826 |

Blending of Normal and CRP-Depleted Sera

The CRP-depleted and normal sera were blended in a range of proportions to obtain low-CRP reference controls at graduated concentration levels. For example, to prepare 1 liter each of controls with target CRP concentrations of 0.3, 0.6, and 0.9 mg/L, CRP-depleted serum in quantities of 725, 450, and 100 mL were mixed with normal serum in quantities of 275, 550, and 900 mL, respectively. The CRP level was determined for each control and where necessary, the CRP concentration in each control was adjusted to the target by adding either further CRP-depleted serum or normal serum. Sodium azide (0.084 mg/dL) was then added to each control, and the controls were mixed for thirty minutes at room temperature, sterile filtered through 0.2-$\mu$m filters, and aseptically placed in sterile glass vials, which were then sealed with sterile stoppers and aluminum crimp seals. The vials were then stored at −10 to −20° C.

Performance of the Controls

Variability of the controls was evaluated by the Dade Behring and Kamiya assays referenced above. Values for the mean, standard deviation (SD), and coefficient of variation (CV) for each of the three levels are listed in Table 3 below.

TABLE 3

Product Variability

| Test Method | Level 1 Mean (mg/L) | SD | % CV | Level 2 Mean (mg/L) | SD | % CV | Level 3 Mean (mg/L) | SD | % CV |
|---|---|---|---|---|---|---|---|---|---|
| Dade Behring | 0.30 | 0 | 0 | 0.59 | 0.03 | 5.1 | 0.91 | 0.03 | 3.3 |
| Kamiya | 0.19 | 0.01 | 5.3 | 0.50 | 0.01 | 2.0 | 0.87 | 0.04 | 4.6 |

The CV values in Table 3 are comparable to those obtained from typical patient samples when tested by hsCRP assays. The controls of this invention thus satisfy one of the most important criteria of a quality control material, which is to be as sensitive to all of the anticipated test and analytical variances as an actual patient sample. Typical hsCRP test kits predict a CV for patient samples of less than 6%.

Stability of the controls under closed-vial conditions was evaluated by an accelerated stability model. In accordance with this model, vials of the controls were stored at 25° C. for different periods of time to observe analyte decomposition or degradation more rapidly than the recommended storage temperature of −10 to −20° C. At the ends of the incubation periods of one, two and three days, the contents of the vials were assayed for CRP concentration. The results are shown in FIG. 1, in which the diamonds represent the Level 1 control, the squares the Level 2, and the triangles the Level 3. The results show that the changes in CRP concentration were either undetectable or insignificant. These results are equivalent to those that would be obtained over a two-year period when stored unopened at −10 to −20° C.

Figure 2:
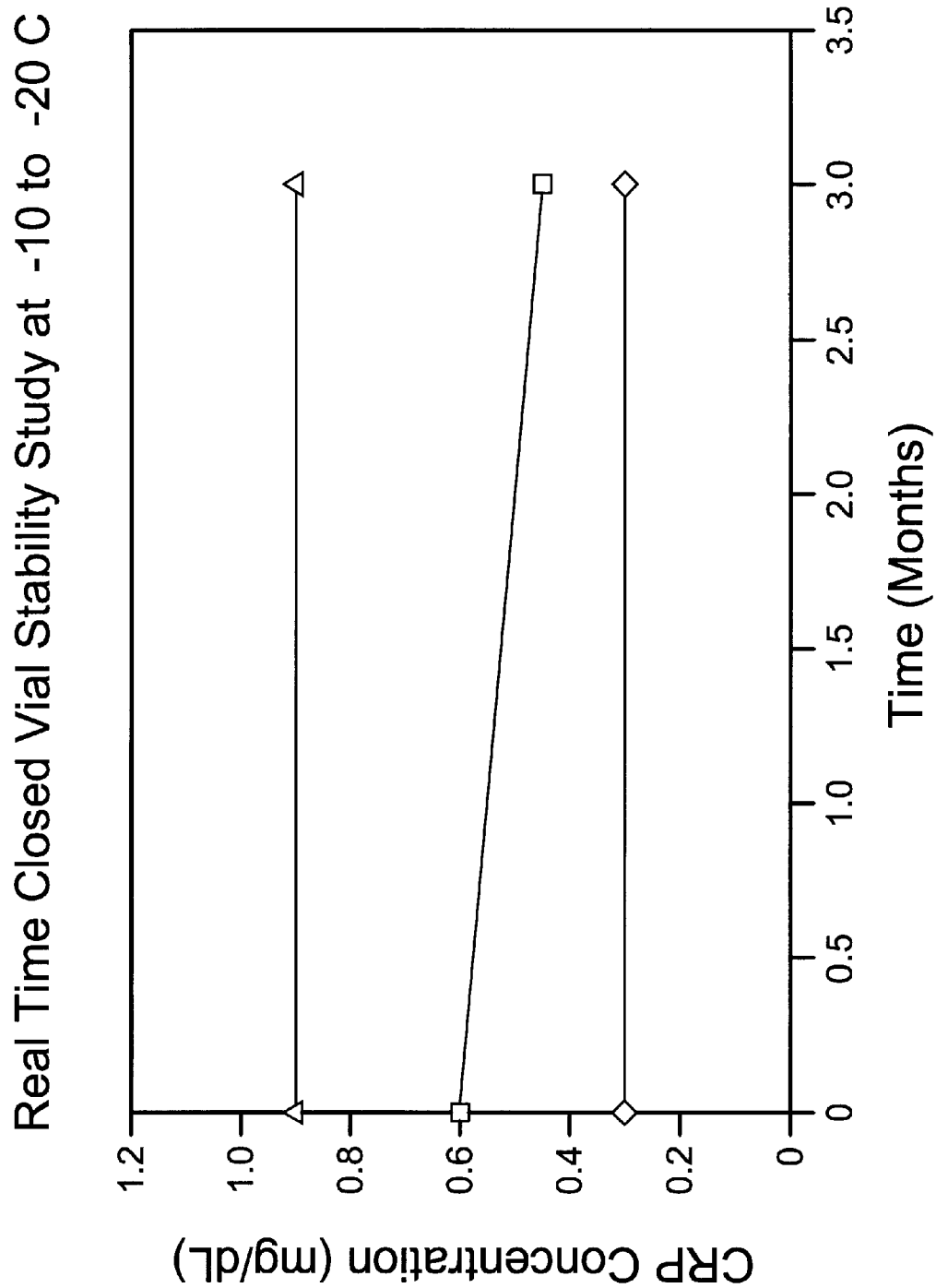
FIG. 2 is a plot of the results of a real-time stability test of controls in accordance with this invention, again taken under closed-vial conditions.

A real-time closed-vial test was performed over an extended period of time by storing the closed vials at −10 to −20° C. Analyses were taken at the start of the test and after three months. The results are shown in FIG. 2, where the symbols are the same as those used in FIG. 1. Here again, the results show that the changes in CRP concentration were either undetectable or insignificant.

Figure 3:
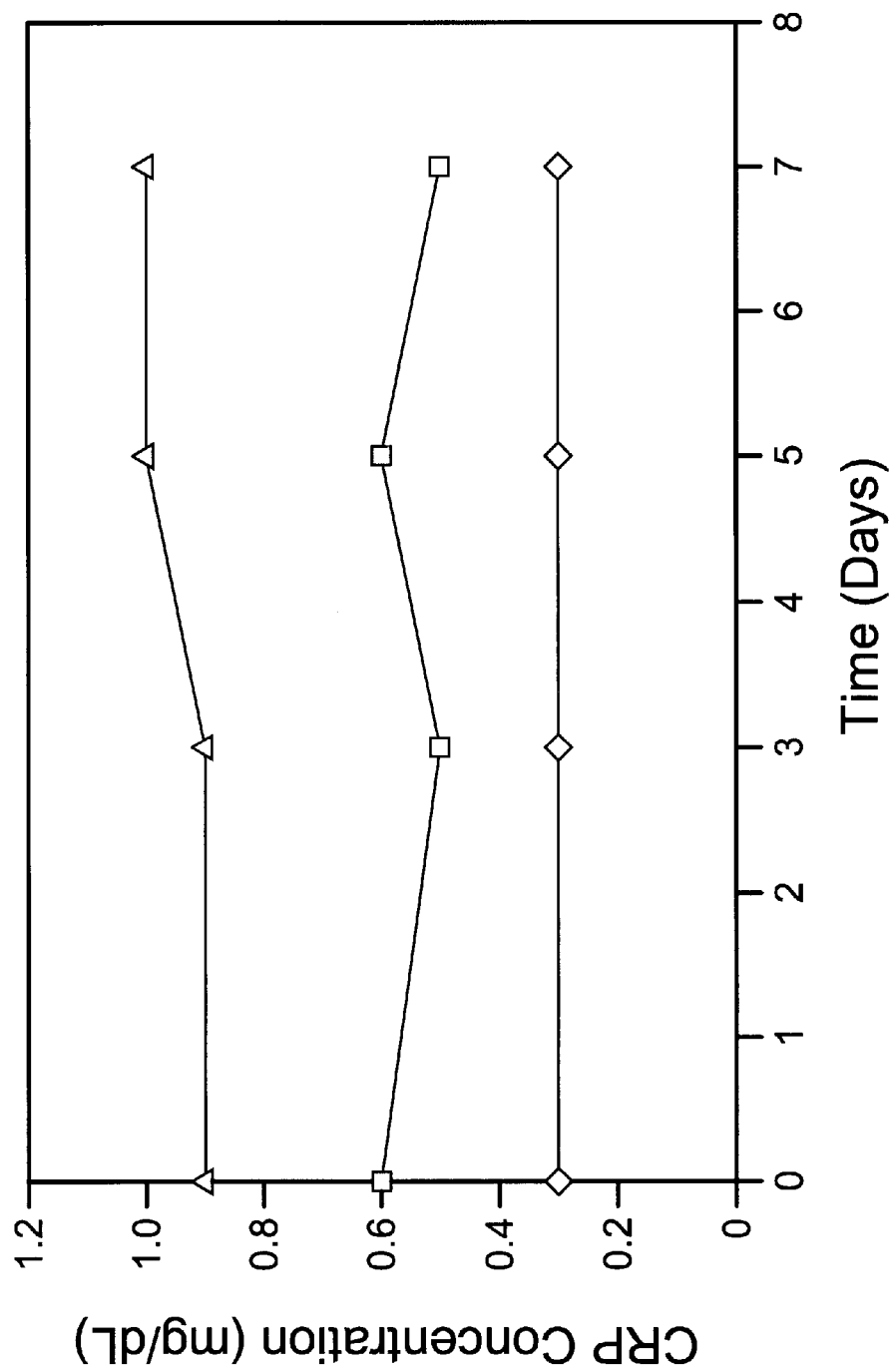
FIG. 3 is a plot of the results of a stability test of controls in accordance with this invention, taken under open-vial conditions.

Stability of the controls under open-vial conditions was evaluated by simulating the conditions under which the controls would actually be used by clinicians. This was done by storing the vials in a refrigerator at 2–8° C. and removing them from the refrigerator once a day for seven consecutive days, allowing them to equilibrate to room temperature for fifteen minutes, then opening the vials and exposing their contents to the laboratory environment, and closing the vials and returning them to the refrigerator. The results for days 3, 5 and 7 are shown in FIG. 3, which indicates that the changes in CRP concentration were either undetectable or insignificant.

The foregoing is offered primarily for purposes of illustration. Those skilled in the art will readily recognize that further variations and modifications can be made without departing from the spirit and scope of the invention.

What is claimed is:

1. A method for preparing a C-reactive protein reference control defined as a fluid having a target C-reactive protein concentration of less than 0.1 mg/L from a sample of human bodily fluid having a total protein concentration of at least about 4.0 g/dL, said method comprising:

(a) adjusting the pH of said sample to a pH within the range of from about 6.5 to about 7.5, when said sample is not within said range, to achieve a substantially neutral sample; and (b) passing said substantially neutral sample through a filter medium selected from the group consisting of precipitated silica, fumed silica, perlite, and precipitated silica, fumed silica, and perlite supported on cellulose, to extract C-reactive protein therefrom by filtration selectively relative to other proteins in said sample and thereby achieve said target C-reactive protein concentration.

2. A method in accordance with claim 1 further comprising adding an antimicrobial agent to the product of step (b).

3. A method in accordance with claim 1 in which said human bodily fluid is a member selected from the group consisting of blood, serum, and plasma.

4. A method in accordance with claim 1 in which said human bodily fluid is a member selected from the group consisting of serum and plasma.

5. A method in accordance with claim 1 in which silica-containing filter medium is a member selected from the group consisting of fumed silica and perlite.

6. A method in accordance with claim 1 in which silica-containing filter medium is a member selected from the group consisting of fumed silica and perlite, supported on cellulose.

7. A method in accordance with claim 1 in which said target C-reactive protein concentration is less than 0.05 mg/L.

8. A method in accordance with claim 1 in which said target C-reactive protein concentration is between 0.01 mg/L and 0.05 mg/L.

* * * * *